United States Patent
Schroeder

(10) Patent No.: US 11,596,471 B2
(45) Date of Patent: Mar. 7, 2023

(54) TRACKING CATHETERS BASED ON A MODEL OF AN IMPEDANCE TRACKING FIELD

(71) Applicant: Boston Scientific Scimed, Inc., Maple Grove, MN (US)

(72) Inventor: Tobias Schroeder, Melrose, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 334 days.

(21) Appl. No.: 16/824,154

(22) Filed: Mar. 19, 2020

(65) Prior Publication Data
US 2020/0297413 A1   Sep. 24, 2020

Related U.S. Application Data

(60) Provisional application No. 62/822,351, filed on Mar. 22, 2019.

(51) Int. Cl.
*A61B 34/20* (2016.01)
*A61B 18/14* (2006.01)
(Continued)

(52) U.S. Cl.
CPC .......... *A61B 18/1492* (2013.01); *A61B 18/02* (2013.01); *A61B 2018/00577* (2013.01);
(Continued)

(58) Field of Classification Search
CPC .. A61B 2018/0212; A61B 2018/00892; A61B 2018/00875; A61B 2018/00839;
(Continued)

(56) References Cited

U.S. PATENT DOCUMENTS 8,456,182 B2    6/2013  Bar-Tal et al.
2002/0072686 A1*  6/2002  Hoey .................. A61B 5/4893
                                                    600/587

(Continued)

OTHER PUBLICATIONS

International Search Report and Written Opinion received for PCT Patent Application No. PCT/US2020/023636, dated Jun. 26, 2020, 19 pages.

*Primary Examiner* — Khadijeh A Vahdat
(74) *Attorney, Agent, or Firm* — Nelson Mullins Riley & Scarborough LLP

(57) ABSTRACT

A system for tracking a catheter in a patient. The system including a plurality of surface electrodes and a surface patch attached to the patient and a processor coupled to the plurality of surface electrodes and the surface patch. The processor determines a location of at least one of the plurality of surface electrodes, stores locations of the surface patch and the at least one of the plurality of surface electrodes, determines a three-dimensional shell shape that corresponds to a portion of the patient, determines a model of an impedance tracking field in at least a portion of the three-dimensional shell shape, injects current through one or more of the plurality of surface electrodes, fits measured voltages from the catheter to the model of the impedance tracking field to determine locations of the catheter, and provides therapy to the patient based on the locations of the catheter.

17 Claims, 5 Drawing Sheets

(51) Int. Cl.
*A61B 18/02* (2006.01)
*A61B 18/00* (2006.01)

(52) U.S. Cl.
CPC ............. *A61B 2018/00839* (2013.01); *A61B 2018/00875* (2013.01); *A61B 2018/00892* (2013.01); *A61B 2018/0212* (2013.01)

(58) Field of Classification Search
CPC .......... A61B 2018/00577; A61B 18/02; A61B 18/1492; A61B 2017/00243; A61B 2034/2053; A61B 2034/2068; A61B 34/20; A61B 2090/0818; A61B 5/0536; A61B 5/0538; A61B 5/062; A61B 5/063; A61B 5/6852
USPC ........................................................ 600/509
See application file for complete search history.

(56) References Cited

U.S. PATENT DOCUMENTS

| | | | | |
|---|---|---|---|---|
| 2009/0306497 | A1* | 12/2009 | Manzke | A61B 8/0841 600/424 |
| 2010/0030061 | A1* | 2/2010 | Canfield | A61B 6/032 600/413 |
| 2010/0036227 | A1* | 2/2010 | Cox | A61B 8/0833 600/509 |
| 2014/0187905 | A1 | 7/2014 | Olson | |
| 2014/0276746 | A1* | 9/2014 | Nabutovsky | A61B 5/0538 606/33 |
| 2014/0343650 | A1 | 11/2014 | Rosenberg et al. | |
| 2015/0141798 | A1 | 5/2015 | Bar-Tal | |
| 2017/0065204 | A1* | 3/2017 | Ludwin | A61B 5/063 |

\* cited by examiner

TRACKING CATHETERS BASED ON A MODEL OF AN IMPEDANCE TRACKING FIELD

CROSS REFERENCE TO RELATED APPLICATION

This application claims priority to Provisional Application No. 62/822,351, filed Mar. 22, 2019, which is herein incorporated by reference in its entirety.

TECHNICAL FIELD

The present disclosure relates to systems and methods for tracking catheters in a patient and, more particularly, to systems and methods for tracking catheters without first mapping a region of interest in the patient. The disclosure further relates to systems and methods for tracking catheters based on fitting measured voltages to a model of an impedance tracking field in the region of interest in the patient.

BACKGROUND

Some mapping systems provide impedance tracking functionality for navigating catheters in a patient's body. Typically, in these systems, impedance tracking functionality relies on injecting current into electrodes, such that an electric field is generated in the patient. To determine a catheter's location, the electric field distribution in a region of interest, such as inside the heart, is mapped with a dedicated mapping catheter. This mapping catheter may be a magnetically tracked mapping catheter that measures the impedance tracking field in the region of interest. Magnetically tracked locations of the catheter and field voltages measured by the catheter are used to create a map of the region of interest. The system stores the collected data in a map that may include one or more look-up tables of the measured field voltages. To navigate a catheter in the region of interest, field voltages are measured by the catheter and compared to the one or more look-up tables.

Rather than using mapped impedance tracking field information, some systems rely on pairs of electrodes, each placed on opposing sides of the patient's body. The electrode pairs are positioned to generate fields that are approximately orthogonal to each other, such that catheter tracking assumes orthogonal fields.

In other systems, x-ray fluoroscopy is used to navigate catheters in a patient. In x-ray fluoroscopy, a continuous x-ray image is produced and displayed on a monitor by passing x-ray beams through the body. In some procedures, fluoroscopy may be combined with an impedance tracking method, such as the impedance tracking method described above, to navigate the catheter in the patient's body.

The need to first create a map of the impedance tracking field in the region of interest and/or using x-ray fluoroscopy presents disadvantages. One disadvantage is navigating catheters in patients in less complex procedures, where the less complex procedures do not justify the time or money needed for mapping the region of interest. Another disadvantage is exposing patients to excessive x-rays in fluoroscopy procedures, where physicians and/or medical personnel want to reduce exposure to x-rays.

Also, systems employing orthogonal electrode pairs increase cost and complexity of the procedure and equipment, since additional electrode surface patches and corresponding system connectivity are needed. Moreover, assumptions of field orthogonality provide only limited accuracy since the exact electrode locations remains unknown.

SUMMARY

In an Example 1, a system for tracking a catheter in a patient including a plurality of surface electrodes attached to the patient, a surface patch attached to the patient, and a processor coupled to the plurality of surface electrodes and the surface patch. The processor is configured to: determine a location of at least one of the plurality of surface electrodes; store a location of the surface patch and the location of the at least one of the plurality of surface electrodes; determine a three-dimensional shell shape that corresponds to a portion of the patient; determine a model of an impedance tracking field in at least a portion of the three-dimensional shell shape; inject current through one or more of the plurality of surface electrodes to create an electric field in the patient; fit measured voltages from the catheter to the model of the impedance tracking field to determine locations of the catheter in the patient; and provide therapy to the patient based on the locations of the catheter.

In an Example 2, the system of Example 1, wherein the plurality of surface electrodes is a plurality of electrocardiogram electrodes attached to the patient.

In an Example 3, the system of any of Examples 1 and 2, wherein the surface patch is a surface back patch that includes a magnetic tracking system that provides location information about the location of the surface back patch attached to the back of the patient.

In an Example 4, the system of any of Examples 1-3, including a stylus that is enabled for tracking a location of the stylus, wherein the processor is coupled to the stylus and configured to determine the location of the at least one of the plurality of surface electrodes by receiving location information from the stylus when the stylus is touching the electrode.

In an Example 5, the system of any of Examples 1-4, wherein the processor is configured to determine the three-dimensional shell shape based on one or more of an ovoid shape, the location of the surface patch and the location of the at least one of the plurality of surface electrodes, locations of multiple points on surfaces of the patient, and anatomical landmarks in the patient.

In an Example 6, the system of any of Examples 1-5, wherein the processor is configured to determine the model of the impedance tracking field based on estimates of electromagnetic tissue properties of the patient that are based on at least one of constant gradients across the patient, estimates of locations of organs in the patient, and electrical impedance tomography imaging of the patient.

In an Example 7, the system of any of Examples 1-6, wherein the processor is configured to refine the model of the impedance tracking field based on at least one of measured voltages from a tracking catheter and magnetically obtained locations of the tracking catheter in the patient.

In an Example 8, the system of any of Examples 1-7, wherein the processor is configured to provide respiration gating to fit the measured voltages from the catheter to the model of the impedance tracking field to determine the locations of the catheter in the patient.

In an Example 9, a method of tracking a catheter including: determining, by a processor, a location of at least one of a plurality of surface electrodes attached to a patient; storing, by the processor, the location of the at least one of the plurality of surface electrodes; storing, by the processor, a location of a surface patch attached to the patient; determining, by the processor, a three-dimensional shell shape that corresponds to a portion of the patient; determining, by the processor, a model of an impedance tracking field in at least a portion of the three-dimensional shell shape; injecting, by the processor, current to one or more of the plurality of surface electrodes to create an electric field in the patient; fitting, by the processor, measured voltages from the catheter to the model of the impedance tracking field to track locations of the catheter in the patient; and providing, by the processor, therapy to the patient based on the locations of the catheter.

In an Example 10, the method of Example 9, wherein storing the location of the surface patch includes obtaining location information from a tracking system in a surface back patch, and wherein determining the location of the at least one of a plurality of surface electrodes includes determining, by the processor, a location of at least one of a plurality of electro-cardiogram electrodes attached to the patient.

In an Example 11, the method of any of Examples 9 and 10, including receiving location information from a stylus that is enabled for tracking a location of the stylus, in determining the location of the at least one of a plurality of surface electrodes.

In an Example 12, the method of Example 11, wherein determining, by the processor, the three-dimensional shell shape includes determining the three-dimensional shell shape based on one or more of the location of the surface patch and the location of the at least one of the plurality of surface electrodes determined from location information received from the stylus, locations of multiple points on surfaces of the patient determined from location information received from the stylus, and locations of anatomical landmarks in the patient determined from location information received from the stylus.

In an Example 13, the method of any of Examples 9-12, wherein determining, by the processor, the three-dimensional shell shape includes determining the three-dimensional shell shape based on one or more of an ovoid shape, the location of the surface patch and the location of the at least one of the plurality of surface electrodes, locations of multiple points on surfaces of the patient, and anatomical landmarks in the patient.

In an Example 14, the method of any of Examples 9-13, wherein determining, by the processor, the model of the impedance tracking field in at least a portion of the three-dimensional shell shape, includes determining the model based on estimates of electromagnetic tissue properties of the patient that include one or more of constant gradients across the patient, estimates of locations of organs in the patient, electrical impedance tomography imaging of the patient, such as electrical impedance tomography imaging of the patient based on sensing impedances among electrodes, measured voltages from a tracking catheter and magnetically obtained locations of the tracking catheter in the patient.

In an Example 15, the method of any of Examples 9-14, wherein fitting, by the processor, measured voltages from the catheter to the model of the impedance tracking field includes respiration gating.

In an Example 16, a system for tracking a catheter in a patient including a plurality of surface electrodes attached to the patient, a surface patch attached to the patient, and a processor coupled to the plurality of surface electrodes and the surface patch. The processor configured to: determine a location of at least one of the plurality of surface electrodes; store a location of the surface patch and the location of the at least one of the plurality of surface electrodes; determine a three-dimensional shell shape that corresponds to a portion of the patient; determine a model of an impedance tracking field in at least a portion of the three-dimensional shell shape; inject current through one or more of the plurality of surface electrodes to create an electric field in the patient; fit measured voltages from the catheter to the model of the impedance tracking field to determine locations of the catheter in the patient; and provide therapy to the patient based on the locations of the catheter.

In an Example 17, the system of Example 16, wherein the plurality of surface electrodes is a plurality of electro-cardiogram electrodes attached to the patient.

In an Example 18, the system of Example 16, wherein the surface patch is a surface back patch that includes a magnetic tracking system that provides location information about the location of the surface back patch attached to the back of the patient.

In an Example 19, the system of Example 16, including a stylus that is enabled for tracking a location of the stylus, wherein the processor is coupled to the stylus and configured to determine the location of the at least one of the plurality of surface electrodes by receiving location information from the stylus.

In an Example 20, the system of Example 16, wherein the processor is configured to determine the three-dimensional shell shape based on one or more of an ovoid shape, the location of the surface patch and the location of the at least one of the plurality of surface electrodes, locations of multiple points on surfaces of the patient, and anatomical landmarks in the patient.

In an Example 21, the system of Example 16, wherein the processor is configured to determine the model of the impedance tracking field based on estimates of electromagnetic tissue properties of the patient.

In an Example 22, the system of Example 21, wherein the estimates of electromagnetic tissue properties of the patient are based on at least one of constant gradients across the patient, estimates of locations of organs in the patient, and electrical impedance tomography imaging of the patient.

In an Example 23, the system of Example 21, wherein the processor is configured to refine the model of the impedance tracking field based on at least one of measured voltages from a tracking catheter and magnetically obtained locations of the tracking catheter in the patient.

In an Example 24, the system of Example 16, wherein the processor is configured to receive a system reference voltage that is used to obtain the measured voltages from the catheter, the system reference voltage received from at least one of a reference catheter in the patient, a reference patch attached to the patient, one or more of the plurality of surface electrodes, and the surface patch.

In an Example 25, the system of Example 16, wherein the processor is configured to provide respiration gating to fit the measured voltages from the catheter to the model of the impedance tracking field to determine the locations of the catheter in the patient.

In an Example 26, a system for tracking a catheter in a patient including a plurality of electro-cardiogram electrodes attached to the patient, a surface back patch that includes a magnetic tracking system that provides location information about a location of the surface back patch on the back of the patient, a stylus that is enabled for tracking a location of the stylus; and a processor coupled to the plurality of surface electrodes, the surface back patch, and the stylus. The processor configured to: determine locations of the plurality of electro-cardiogram electrodes from location information obtained from the stylus; determine the location of the surface back patch from the location information from the surface back patch; store the locations of the plurality of electro-cardiogram electrodes and the location of the surface back patch; determine a three-dimensional shell shape that corresponds to a portion of the patient based on the locations of the plurality of electro-cardiogram electrodes and the location of the surface back patch; determine a model of an impedance tracking field in at least a portion of the three-dimensional shell shape; inject current through one or more of the plurality of electro-cardiogram electrodes to create an electric field in the patient; fit measured voltages from the catheter to the model of the impedance tracking field to determine locations of the catheter in the patient; and provide therapy to the patient based on the locations of the catheter.

In an Example 27, the system of Example 26, wherein the processor is configured to determine the three-dimensional shell shape based on one or more of an ovoid shape, locations of multiple points on surfaces of the patient, and anatomical landmarks in the patient.

In an Example 28, the system of Example 26, wherein the processor is configured to determine the model of the impedance tracking field based on estimates of electromagnetic tissue properties of the patient including one or more of constant gradients across the patient, estimates of locations of organs in the patient, and electrical impedance tomography imaging of the patient, such as electrical impedance tomography imaging of the patient using impedance information measured with the plurality of surface electrodes and the surface patch.

In an Example 29, the system of Example 26, wherein the processor is configured to receive a system reference voltage obtained from one or more of a reference catheter in the patient, a reference patch attached to the patient, one or more of the plurality of surface electrodes, and the surface patch.

In an Example 30, a method of tracking a catheter in a patient including: determining, by a processor, a location of at least one of a plurality of surface electrodes attached to the patient; storing, by the processor, the location of the at least one of the plurality of surface electrodes; storing, by the processor, a location of a surface patch attached to the patient; determining, by the processor, a three-dimensional shell shape that corresponds to a portion of the patient; determining, by the processor, a model of an impedance tracking field in at least a portion of the three-dimensional shell shape; injecting, by the processor, current to one or more of the plurality of surface electrodes to create an electric field in the patient; fitting, by the processor, measured voltages from the catheter to the model of the impedance tracking field to track locations of the catheter in the patient; and providing, by the processor, therapy to the patient based on the locations of the catheter.

In an Example 31, the method of Example 30, wherein storing the location of the surface patch includes obtaining location information from a tracking system in a surface back patch, and wherein determining the location of the at least one of a plurality of surface electrodes includes determining, by the processor, a location of at least one of a plurality of electro-cardiogram electrodes attached to the patient.

In an Example 32, the method of Example 30, including receiving location information from a stylus that is enabled for tracking a location of the stylus, in determining the location of the at least one of a plurality of surface electrodes.

In an Example 33, the method of Example 30, wherein determining, by the processor, the three-dimensional shell shape includes determining the three-dimensional shell shape based on one or more of an ovoid shape, the location of the surface patch and the location of the at least one of the plurality of surface electrodes, locations of multiple points on surfaces of the patient, and anatomical landmarks in the patient.

In an Example 34, the method of Example 30, wherein determining, by the processor, the model of the impedance tracking field in at least a portion of the three-dimensional shell shape, includes determining the model based on estimates of electromagnetic tissue properties of the patient that include one or more of constant gradients across the patient, estimates of locations of organs in the patient, electrical impedance tomography imaging of the patient, measured voltages from a tracking catheter and magnetically obtained locations of the tracking catheter in the patient.

In an Example 35, the method of Example 30, wherein the processor is configured to provide respiration gating while obtaining the measured voltages from the catheter.

While multiple embodiments are disclosed, still other embodiments of the present disclosure will become apparent to those skilled in the art from the following detailed description, which shows and describes illustrative embodiments of the disclosure.

Accordingly, the drawings and detailed description are to be regarded as illustrative in nature and not restrictive.

DETAILED DESCRIPTION

Figure 1:
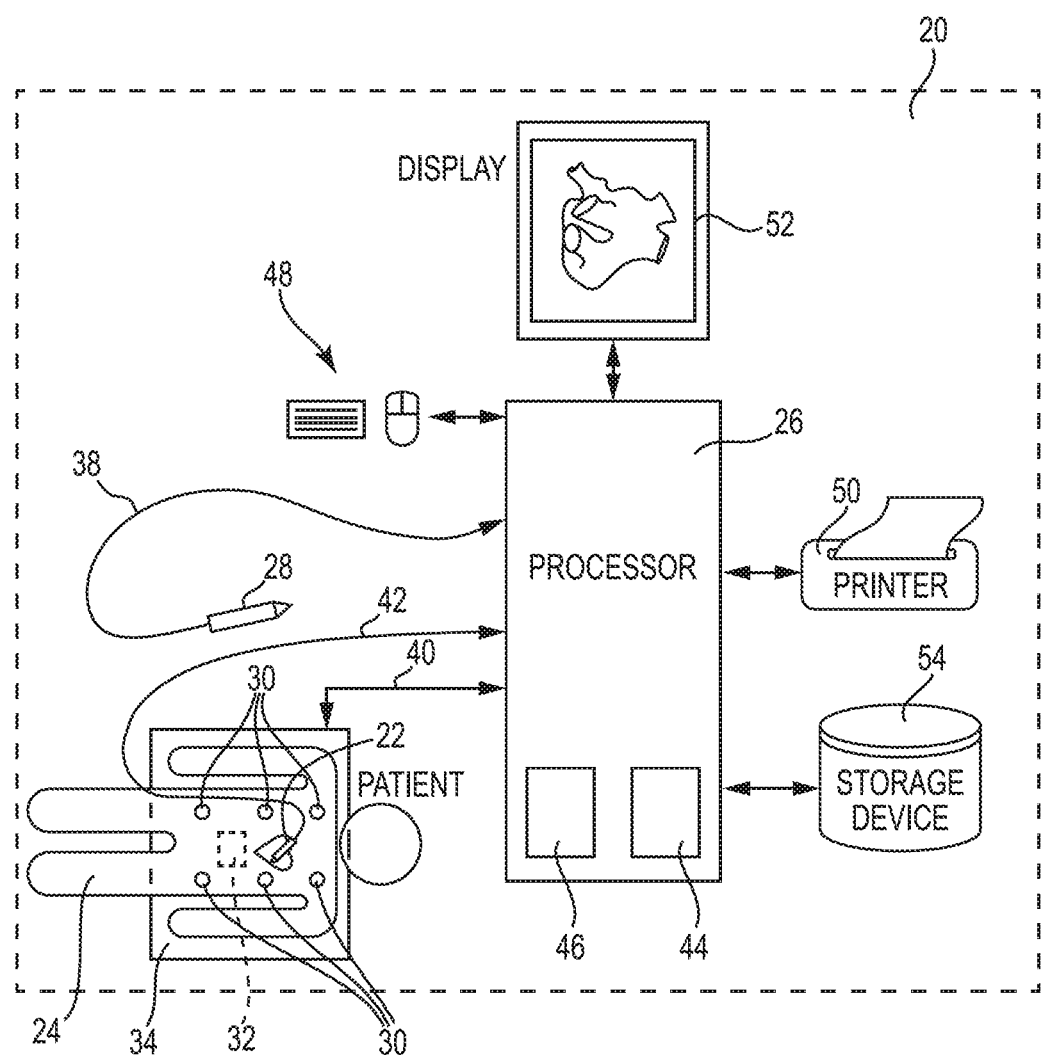
FIG. 1 is a diagram illustrating a system for tracking a catheter (or multiple catheters) in a patient, according to embodiments of the disclosure.

FIG. 1 is a diagram illustrating a system 20 for tracking a catheter 22 (or multiple catheters 22) in a patient 24, according to embodiments of the disclosure. The system 20 is configured to track the catheter 22 in a region of interest, such as the heart, in the patient 24 without first mapping the region of interest. The system 20 is configured to track the catheter 22 based on measuring field voltages in the patient 24 with the catheter 22 and fitting the measured field voltages to a model of an impedance tracking field in the region of interest in the patient 24. In embodiments, the system 20 is used to insert catheters, such as catheter 22, into the heart or a heart cavity of the patient 24.

The system 20 includes a processor 26, a pointer or stylus 28, a plurality of surface electrodes 30, a surface patch 32, the catheter 22 and, in at least some embodiments, a magnet 34. In embodiments, the plurality of surface electrodes 30 are a plurality of electro-cardiogram (ECG) electrodes attached to the patient 24. In some embodiments, the surface patch 32 is a surface back patch attached to the back of the patient 24.

The plurality of surface electrodes 30 and the surface patch 32 are attached to the patient 24 and coupled to the processor 26 by conductive paths (not shown for clarity). The stylus 28 is coupled to the processor 26 by conductive path 38, and the magnet 34 is coupled to the processor 26 by conductive path 40. The catheter 22 is coupled to the processor 26 by conductive path 42. In embodiments, one or more of the processor 26, the stylus 28, the plurality of surface electrodes 30, the surface patch 32, the catheter 22, and the magnet 34 can be coupled to the processor 26 by wireless communications.

The stylus 28 is enabled for tracking a location of the stylus 28 in the system 20. In embodiments, the stylus 28 is enabled for tracking the location of the stylus 28 in relation to one or more of a table the patient 24 is lying on and the magnet 34, or another part of the system 20. In some embodiments, the stylus 28 includes a magnet field tracking system, such that the stylus 28 is enabled for magnetically tracking the location of the stylus 28 in the magnetic field of the magnet 34. In some embodiments, the magnet 34 is an electro-magnet and, in some embodiments, the magnet 34 is controlled by the processor 26.

The processor 26 is configured to receive location information from the stylus 28 to determine the location of the plurality of surface electrodes 30. In embodiments, the processor 26 is configured to activate the magnet 34 and the stylus 28 is configured to provide location information to the processor 26. In some embodiments, each of the plurality of surface electrodes 30 is touched by the stylus 28 and the stylus 28 provides the location information of the stylus 28 to the processor as the stylus 28 is touched to each of the plurality of surface electrodes 30. In embodiments, the processor 26 determines the location of the stylus 28 and the touched surface electrode 30 and stores the location of the touched surface electrode 30.

The processor 26 is further configured to store the location of the surface patch 32. In embodiments, the surface patch 32 is enabled for tracking a location of the surface patch 32 in the system 20. In embodiments, the surface patch 32 is enabled for tracking the location of the surface patch 32 in relation to one or more of a table the patient 24 is lying on and the magnet 34, or another part of the system 20. In some embodiments, the surface patch 32 includes a magnet field tracking system, such that the surface patch 32 is enabled for magnetically tracking the location of the surface patch 32 in the magnetic field of the magnet 34. In embodiments, the processor 26 is configured to activate the magnet 34 and the surface patch 32 is configured to provide location information to the processor 26. In some embodiments, the surface patch 32 is a surface back patch that includes a magnetic tracking system that provides location information about the location of the surface back patch, attached to the back of the patient 24, to the processor 26.

In some embodiments, the stylus 28 is used as described above in relation to the plurality of surface electrodes 30 to obtain the location of the surface patch 32. In embodiments, the stylus 28 touches the surface patch 32 and the processor 26 receives location information from the stylus 28 as it touches the surface patch 32, where the processor 26 determines and stores the location of the surface patch 32.

The processor 26 determines a three-dimensional shell shape that corresponds to a portion of the patient 24. In some embodiments, the processor 26 determines a three-dimensional shell shape that corresponds to the region of interest in the patient 24. In some embodiments, the processor 26 determines a three-dimensional shell shape that corresponds to the thorax region in the patient 24. In embodiments, the processor 26 is configured to determine the three-dimensional shell shape based on one or more of an ovoid shape, the locations of the surface patch 32 and the plurality of surface electrodes 30 on the patient 24, the locations of multiple other points on the surfaces of the patient 24, and anatomical landmarks in the patient 24.

The processor 26 determines a model of an impedance tracking field in at least a portion of this three-dimensional shell shape, based on estimates of electromagnetic tissue properties of the patient 24. In embodiments, these estimates of electromagnetic tissue properties of the patient 24 are based on at least one of constant gradients across the patient 24, estimates of the locations of organs in the patient 24, and electrical impedance tomography (EIT) imaging of the patient 24.

In some embodiments, the processor 26 is configured to refine the model of the impedance tracking field based on location information and measured field voltages received from a tracking catheter in the patient 24. The tracking catheter measures the field voltages of an impedance tracking field that is generated in the patient 24, such as by injecting currents though the plurality of surface electrodes 30 and the patient 24 to the surface patch 32. The processor 32 fits the model of the impedance tracking field to the measured voltages to refine the model. In some embodiments, the tracking catheter is catheter 22. In some embodiments, the tracking catheter includes a magnetic tracking system that provides the location information about the location of the tracking catheter to the processor 26 along with the measured field voltages.

To track a catheter, such as catheter 22, in the region of interest in the patient 24, the processor 26 is configured to inject current through one or more of the plurality of surface electrodes 30 to create an electric field in the patient 24. This electric field is an impedance tracking field that is used to track the location of the catheter 22. In operation, the catheter 22 measures field voltages of the impedance tracking field and the processor 26 fits the measured field voltages from the catheter 22 to the model of the impedance tracking field and determines the location of the catheter 22 in the patient 24.

Also, the processor 26 receives a system reference voltage that is used to obtain the measured field voltages from the catheter 22. In embodiments, the system reference voltage is received from at least one of a reference catheter in the patient 24, a reference patch attached to the patient 24, one or more of the plurality of surface electrodes 30, and the surface patch 32. Also, in some embodiments, the processor 26 is configured to provide respiration gating to fit the measured field voltages from the catheter 22 to the model of the impedance tracking field to determine the locations of the catheter 22 in the patient 24.

The catheter 22 is a moveable catheter 22 having one or more spatially distributed electrodes. The catheter 22 can be used to perform various medical procedures, such as cardiac mapping and/or medical therapeutic treatments including ablation, such as radio frequency (RF) ablation and/or cryogenic ablation. The catheter 22 is used by medical personnel and/or a physician based on the location of the catheter 22 in the patient 24, which was determined by the processor 26.

In some embodiments, the catheter 22 is fitted with various types of electrodes that are configured to perform various functions. For example, the catheter 22 can include at least one pair of current injection electrodes (CIEs) configured to inject electrical current into the medium in which the catheter 22 is disposed. The catheter 22 may also include multiple potential measuring electrodes (PMEs) configured to measure the potentials resulting from the current injected by the current injection electrodes. In some embodiments, the PMEs are used for cardiac mapping. In some embodiments, the relative positions of multiple catheters 22 disposed in the heart of the patient 24 or a cardiac chamber of the heart are determined based on measured field voltages obtained by the PMEs on the catheters 22. In some embodiments, the positions of the catheters 22 can be determined with respect to a surface of the organ, such as the heart of the patient 24.

Further, as to the system 20, the processor 26 is configured to provide and does provide the functions of the system 20. The processor 26 is a processor-based device that includes one or more computers, micro-processors, and/or other types of processor-based devices suitable for multiple applications. The processor 26 can include volatile and/or non-volatile memory elements 44, and peripheral devices to enable input/output functionality. The peripheral devices can include, for example, a CD-ROM drive, a floppy drive, and/or a network connection for downloading related content to the processor 26. Such peripheral devices may also be used for downloading software containing computer instructions to enable operation of the processor 26, and for downloading software implemented programs to perform the operations of the system 20. The processor 26 may be implemented on a single or multiple processor-based platform capable of performing the functions of the system 20. Additionally, one or more of the procedures performed by the processor 26 may be implemented using processing hardware such as digital signal processors (DSPs), field programmable gate arrays (FPGAs), mixed-signal integrated circuits, and application specific integrated circuits (ASICs).

In embodiments, the processor 26 includes an electronics module 46 that is coupled to one or more of the stylus 28, the plurality of surface electrodes 30, the surface patch 32, and the catheter 22, to receive signals from and provide signals to the one or more of the stylus 28, the plurality of surface electrodes 30, the surface patch 32, and the catheter 22. The electronics module 46 can include a signal generation module for injecting current into the region of interest, such as the heart cavity, through the surface electrodes 30. The electronics module 46 can also include a signal acquisition module for measuring potentials through the surface electrodes 30 and/or through the electrodes of the catheter 22, such as the PMEs. The electronics module 46 may further include a signal acquisition module for receiving the location information from the stylus 28 and/or the location information from the surface patch 32. In embodiments, the electronics module 46 is used for one or more of sampling, sensing, filtering, and amplifying received signals.

The electronics module 46 can be implemented using analog or digital electronics, or a combination of both. In some embodiments, the electronics module 46 is implemented by use of integrated components on a dedicated printed circuit board. In some embodiments, at least some of the signal conditioning tasks are implemented by one or more of a central processing unit (CPU), an FPGA and a DSP. In some embodiments, the electronics module 46 is implemented using analog hardware augmented with signal processing capabilities provided by CPU, FPGA and DSP devices.

As illustrated in FIG. 1, the system 20 further includes input/output devices 48, such as a mouse and a keyboard, a printer 50, and a display device 52 that may include a touch screen. Also, the system 20 includes a storage device 54 that is used to store data acquired by the processor 26. The input/output devices 48, the printer 50, the display device 52, and the storage device 54 are each communicatively coupled to the processor 26, such as by a wired connection or wirelessly.

The processor 26 can access one or more input devices to obtain input data, and one or more output devices to communicate output data. In embodiments, the input/output devices 48 include one or more of the following: random access memory (RAM), a redundant array of independent disks (RAID), a floppy drive, a compact disc (CD) drive, a DVD drive, a magnetic disk, an internal hard drive, an external hard drive, a memory stick, and other storage devices capable of being accessed by the processor 26, where such aforementioned examples are not exhaustive, and are for illustration and not limitation.

The systems and methods described herein are not limited to one hardware/software configuration. The systems and methods can be implemented in hardware, or a combination of hardware and software, and/or can be implemented from commercially available modules, applications, and devices. Where the systems and methods described herein are at least partly based on the use of computers, micro-processors and/or other computing devices, the systems and methods can be implemented in one or more computer programs, where a computer program can be understood to include one or more processor executable instructions. The computer programs can execute on processor 26, and can be stored on one or more storage mediums, such as the memory elements 44 and the storage device 54, which are readable by the processor 26.

In addition, the computer programs can be implemented using one or more high level procedural or object-oriented programming languages to communicate with a computer system and/or the computer programs can be implemented in assembly or machine language. The language can be compiled or interpreted. Devices and/or computer systems that integrate with the processor 26 can include, for example, a personal computer, a workstation (e.g., Sun, HP), a personal digital assistant (PDA), a handheld device such as cellular telephone, laptop, handheld, or another device capable of being integrated with a processor. Accordingly, the devices provided herein are not exhaustive and are provided for illustration and not limitation.

Also, throughout this disclosure references to "a micro-processor" and "a processor", or "the micro-processor" and "the processor," can be understood to include one or more micro-processors and/or processors that can communicate in a stand-alone and/or a distributed environment and can thus be configured to communicate via wired or wireless communications with other processors. Furthermore, references to memory, unless otherwise specified, can include one or more processor-readable and accessible memory elements and/or components that can be internal to the processor device, and/or external to the processor device, and accessed via a wired or wireless network using a variety of communications protocols, and unless otherwise specified, can be arranged to include a combination of external and internal memory devices, where such memory can be contiguous and/or partitioned based on the application. Accordingly, references to a database can be understood to include one or more memory associations, where such references can include commercially available database products (e.g., SQL, Informix, Oracle) and/or proprietary databases, and may also include other structures for associating memory such as links, queues, graphs, trees, with such structures provided for illustration and not limitation.

Figure 2:
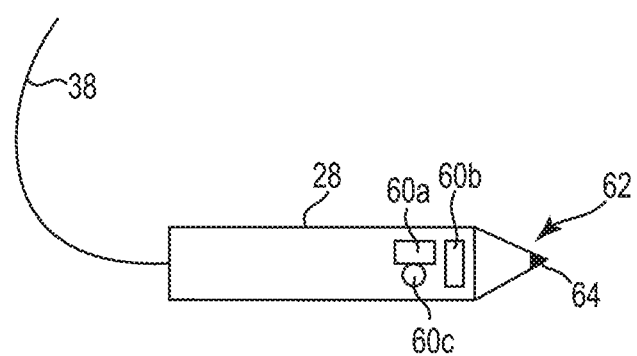
FIG. 2 is a diagram illustrating one example of a stylus that is enabled for tracking the location of the stylus in the system, according to embodiments of the disclosure.

FIG. 2 is a diagram illustrating one example of a stylus 28 that is enabled for tracking the location of the stylus 28 in the system 20, according to embodiments of the disclosure. In embodiments, the stylus 28 is configured for determining six degrees of freedom in a six degrees of freedom electromagnetic tracking system. Also, in embodiments, the stylus 28 is at least one of non-sterile and reusable.

In the example embodiments described herein, the stylus 28 includes three magnetic tracking coils 60a-60c for determining the location of the stylus 28 in the magnetic tracking field (or fields) generated by the magnet 34. In other example embodiments, the stylus 28 includes only two magnetic coils for determining six degrees of freedom. In some example embodiments, the stylus 28 includes only two magnetic coils for determining six degrees of freedom, where the two magnetic coils are not orthogonal or parallel to one another.

In the present example, the three magnetic coils 60a-60c are situated at the distal end 62 or toward the distal end 62 of the stylus 28. The three magnetic coils 60a-60c are oriented orthogonal to one another, such that one coil is situated in each of the three x-y-z axis directions. Each of the three magnetic tracking coils 60a-60c is electrically coupled to the processor 26, such as by a separate wire, in conductive path 38. The stylus 28 and the connecting conductive path 38 are long enough to reach each of the surface electrodes 30 while the magnetic tracking coils 60a-60c are maintained inside the magnetic tracking field created by the magnet 34. In some embodiments, the three magnetic coils 60a-60c are not oriented orthogonal to one another. Also, in other embodiments, the stylus 28 includes less than three magnetic coils 60a-60c or more than three magnetic coils 60a-60c, where the less than three magnetic coils and the more than three magnetic coils can be orthogonal or not orthogonal to one another.

In operation, the processor 26 activates the magnet 34 to generate a magnetic tracking field (or fields) and each of the three magnetic tracking coils 60a-60c transmits a signal that corresponds to the magnetic tracking field(s) back to the processor 26. The processor 26 receives the signals and determines the location of the stylus 28 in the magnetic tracking field and in relation to the system 20, such as in relation to one or more of the table the patient 24 is lying on and the magnet 34, or another part of the system 20.

In some embodiments, the stylus 28 includes a distal tip 64 that can be depressed, such as by touching an electrode, and the stylus 28 transmits a signal to the processor 26 in response to the distal tip 64 being depressed. This signal can be used, by the processor 26, to indicate that the signals currently being transmitted by the magnetic tracking coils 60a-60c are to be used to determine the location of the stylus 28. Also, in some embodiments, the distal tip 64 of the stylus 28 can be depressed and the stylus 28 transmits one or more of a separate signal to the processor 26 in response to the distal tip 64 being depressed and the signals from the magnetic tracking coils 60a-60c to be used to determine the location of the stylus 28. In other embodiments, the stylus 28 can be otherwise configured, such as by using capacitance or inductance, to indicate that the stylus 28 has been touched to an object, such as an electrode.

Figures 3A, 3B:
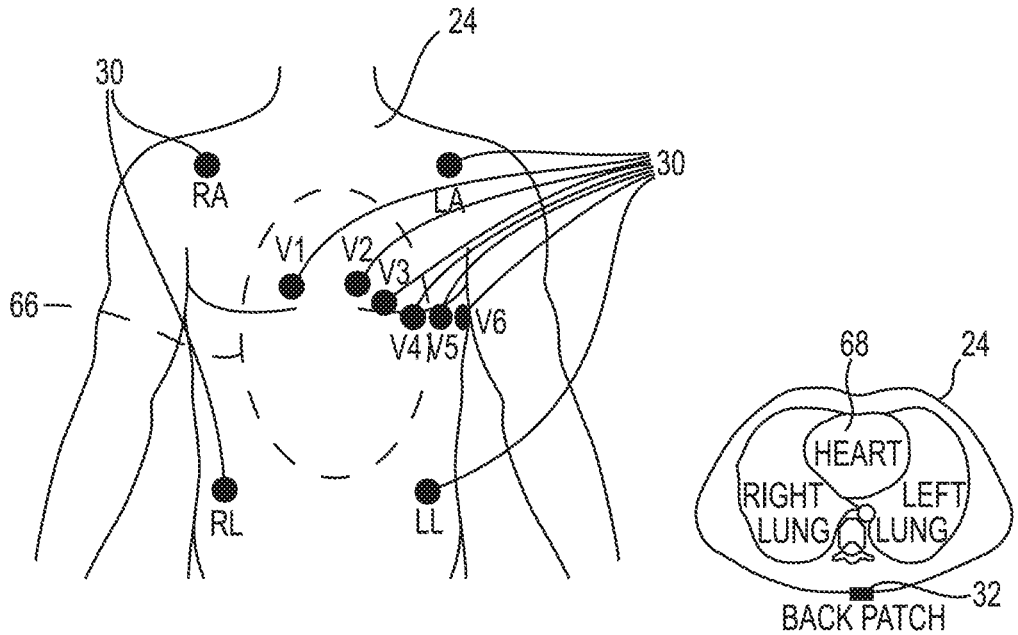
FIG. 3A is a diagram illustrating the plurality of surface electrodes attached to the patient and a three-dimensional shell shape, depicted in dashed lines, that corresponds to a portion of the patient, according to embodiments of the disclosure.
FIG. 3B is a diagram illustrating the surface patch attached to the patient, according to embodiments of the disclosure.

FIGS. 3A and 3B are diagrams illustrating the plurality of surface electrodes 30 and the surface patch 32 attached to the patient 24, according to embodiments of the disclosure.

FIG. 3A is a diagram illustrating the plurality of surface electrodes 30 (also labeled as RA, LA, RL, LL, V1, V2, V3, V4, V5 and V6) attached to the patient 24 and a three-dimensional shell shape 66, depicted in dashed lines, that corresponds to a portion of the patient 24, according to embodiments of the disclosure. In this example, the plurality of surface electrodes 30 are a plurality of ECG electrodes 30 attached to the patient 24. In embodiments, the plurality of ECG electrodes 30 includes 10 electrodes. In other embodiments, the plurality of ECG electrodes 30 includes more than 10 electrodes, such as 12 or more electrodes. In some embodiments, the plurality of ECG electrodes 30 includes less than 10 electrodes.

To obtain the locations of the plurality of ECG electrodes 30 attached to the patient 24, at least one of the plurality of ECG electrodes 30 is touched by the stylus 28 and the stylus 28 provides the signals from the three magnetic tracking coils 60a-60c to the processor 26. The stylus 28 is touched to the at least one of the plurality of ECG electrodes 30 by one or more medical personnel, such as a physician, a nurse, and/or a mapping specialist. In embodiments, the stylus 28 also provides the separate signal that indicates the stylus 28 has been touched to one of the plurality of ECG electrodes 30 and the processor 26 uses this signal to indicate that the signals transmitted by the magnetic tracking coils 60a-60c are to be used to determine the location of the stylus 28. In some embodiments, the locations of other electrodes of the plurality of ECG electrodes 30 are calculated or determined from the location of the at least one of the plurality of ECG electrodes 30 as determined above.

In embodiments, to obtain the location of each of the plurality of ECG electrodes 30 attached to the patient 24, each of the plurality of ECG electrodes 30 is touched by the stylus 28 and the stylus 28 provides the signals from the three magnetic tracking coils 60a-60c to the processor 26 as each of the plurality of ECG electrodes 30 is touched. In embodiments, the stylus 28 provides the separate signal that indicates the stylus 28 is being touched to one of the plurality of ECG electrodes 30, as each of the plurality of ECG electrodes 30 is touched.

The processor 26 receives the signals from the stylus 28 and determines the location of the stylus 28 and the touched ECG electrode 30. The processor 26 then stores the location of the stylus 28 and the touched ECG electrode 30.

FIG. 3B is a diagram illustrating the surface patch 32 attached to the patient 24, according to embodiments of the disclosure. In this example, the surface patch 32 is a back patch 32 attached to the back of the patient 24. The back patch 32 is configured for magnetically tracking the location of the back patch 32 in the magnetic tracking field of the magnet 34. In embodiments, the back patch 32 is configured for magnetically tracking 5 or 6 degrees of freedom in the magnetic tracking field of the magnet 34. In some embodiments, the back patch 32 includes one magnetic tracking coil for determining five degrees of freedom. In some embodiments, the back patch 32 includes two magnetic tracking coils for determining six degrees of freedom. In some embodiments, the back patch 32 includes three magnetic tracking coils for determining six degrees of freedom. In some embodiments, the back patch 32 includes two magnetic coils for determining six degrees of freedom, where the two magnetic coils are not orthogonal or parallel to one another. In some embodiments, the back patch 32 includes three magnetic tracking coils like the three magnetic tracking coils 60a-60c described above for the stylus 28.

The back patch 32 is enabled for tracking the location of the back patch 32 in relation to one or more of the table the patient 24 is lying on and the magnet 34, or another part of the system 20. In some embodiments, the two or three magnetic coils are not oriented orthogonal to one another. Also, in other embodiments, the back patch 32 includes less than three magnetic coils or more than three magnetic coils.

To obtain the location of the back patch 32, the processor 26 activates the magnet 34 and the back patch 32 provides signals from the magnetic coils to provide location information to the processor 26. The processor 26 receives the signals from the back patch 32 and determines the location of the back patch 32. The processor 26 then stores the location of the back patch 32.

Also, in some embodiments, shifts in the position and/or orientation of the back patch 32 represent shifts in the position of the patient 24. These shifts in the position of the patient 24 are detected using the back patch 32 and used by the processor 26 to compensate the tracked positions or locations of, for example, the catheter 22. Where, the back patch 32 is used as the impedance tracking space reference. Thus, if the patient 24 moves with respect to the magnetic tracking reference frame, the movement is detected, and a mathematical correction is applied, such that the impedance tracked and/or magnetically tracked catheter 22 remains in the same coordinate frame.

In some embodiments, the stylus 28 is used as described above in relation to the plurality of ECG electrodes 30 to obtain the location of the back patch 32. In embodiments, the stylus 28 is touched to the back patch 32 and the processor 26 receives location information from the stylus 28 as it touches the back patch 32. The processor 26 then determines the location of the stylus 28 and the back patch 32 and stores the location of the stylus 28 and the back patch 32.

After the locations of the at least one or all of the plurality of ECG electrodes 30 and the back patch 32 are known and recorded, the processor 26 determines the three-dimensional shell shape 66 and a mathematical model of an electric field through the three-dimensional shell shape 66. In the current example, the three-dimensional shell shape 66 corresponds to the thorax region in the patient 24, which includes the heart of the patient 24.

The processor 26 determines the three-dimensional shell shape 66. In some embodiments, the processor 26 determines the three-dimensional shell shape 66 to be a simple ovoid shape, with little or no scaling of the ovoid shape. In some embodiments, the processor 26 determines the three-dimensional shell shape 66 using an optimization algorithm to scale the ovoid shape to a best fit inside the locations of the at least one or all of the plurality of ECG electrodes 30 and the back patch 32.

In some embodiments, the processor 26 fits the three-dimensional shell shape 66 to the locations of the at least one or all of the plurality of ECG electrodes 30 and the back patch 32. In some embodiments, the processor 26 determines the three-dimensional shell shape 66 using an optimization algorithm to obtain a best fit to the locations of the at least one or all of the plurality of ECG electrodes 30 and the back patch 32. In some embodiments, the processor 26 determines the three-dimensional shell shape 66 using a three-dimensional fitting algorithm to fit the three-dimensional shell shape 66 to the locations of the at least one or all of the plurality of ECG electrodes 30 and the back patch 32.

In some embodiments, the stylus 28 is used to scribe points along the surface of the patient 24, where the processor 26 records the locations of the scribed points and fits the three-dimensional shell shape 66 to the locations of the scribed points and the locations of the at least one or all of the plurality of ECG electrodes 30 and the back patch 32. In some embodiments, the processor 26 fits the three-dimensional shell shape 66 to the locations of the scribed points and the locations of the at least one or all of the plurality of ECG electrodes 30 and the back patch 32, using one or more of an optimization algorithm to obtain a best fit and a three-dimensional fitting algorithm.

In some embodiments, anatomical landmarks are identified in or on the patient 24, such as by EIT or using the stylus 28, and the processor 26 fits the three-dimensional shell shape 66 to the anatomical landmarks and the locations of the at least one or all of the plurality of ECG electrodes 30 and the back patch 32. In some embodiments, the stylus 28 is used to identify anatomical landmarks in the patient 24, where the processor 26 records the locations of the anatomical landmarks and fits the three-dimensional shell shape 66 to the locations of the anatomical landmarks and the locations of the at least one or all of the plurality of ECG electrodes 30 and the back patch 32. In some embodiments, the processor 26 fits the three-dimensional shell shape 66 to the anatomical landmarks and the locations of the at least one or all of the plurality of ECG electrodes 30 and the back patch 32, using one or more of an optimization algorithm to obtain a best fit and a three-dimensional fitting algorithm.

Next, the processor 26 records the locations of the plurality of ECG electrodes 30 as current injection points and determines the model of the impedance tracking field in the three-dimensional shell shape 66, which corresponds to the thorax region of the patient 24 including the heart of the patient 24. The processor 26 determines the model of the impedance tracking field based on estimates of the electromagnetic tissue properties in the region of interest, in this example the thorax, of the patient 24.

The electromagnetic tissue properties have an impact on the voltage distribution inside the body. Parameters such as conductivity σ (r) and permittivity ∈ (r) are different among tissue types, see Table 1.

TABLE 1

Electromagnetic tissue properties at 13027 Hz [4].

| Tissue | Conductivity σ (S/m) | Rel. permittivity e |
|---|---|---|
| Blood | 0.70006 | 5244.7 |
| Blood vessel | 0.31368 | 5801.9 |
| Bone Cancellous | 0.082745 | 1353.4 |
| Bone Cortical | 0.020461 | 447.47 |
| Fat | 0.023906 | 771.97 |
| Heart | 0.16092 | 55136 |
| Lung deflated | 0.24592 | 26647 |
| Lung inflated | 0.094678 | 13412 |

Depending on the tracking field model accuracy needs, an assumption of uniform tissue properties can be used. Alternatively, the model can contain different tissue regions based on a shape atlas of common human anatomical data. This atlas is then scaled based on the approximated thorax shape.

In a further refinement, a dedicated driving pattern of available surface electrodes 30 can provide input data to an optimization routine to adjust tissue type distribution, in a method akin to EIT.

Also, a related parameter to include in the model is the impedance of the electrode-skin interface. This impedance can be determined by driving a current from one ECG electrode 30 and sinking it to an adjacent ECG electrode 30. Analyzing the resulting voltage drop can provide an estimate of skin-to-electrode interface and underlying tissue impedance.

In embodiments, the estimates of the electromagnetic tissue properties of the patient 24 are based on constant gradients across the thorax of the patient 24, without considering different tissue properties. In some embodiments, the estimates of the electromagnetic tissue properties of the patient 24 are based on estimates of the locations of organs, such as the heart and lungs, in the thorax of the patient 24, where the organs are scaled internally as the three-dimensional shell shape 66 is scaled externally. In some embodiments, the estimates of the electromagnetic tissue properties of the patient 24 are based on EIT imaging of the patient 24.

In embodiments, the distal tip 64 of the stylus 28 includes a stylus tip electrode that makes electrical contact with the skin of the patient 24. The stylus tip electrode is configured as a voltage sensing and a current driving electrode. In embodiments, the stylus 28 transmits one or more separate signals to the processor 26 in response to the stylus tip electrode touching the skin of the patient 24. The signals are used to determine the location of the stylus 28.

In embodiments, the user touches a number of skin surface points of the patient 24 around an anatomical region of interest and the system records the locations of the stylus tip electrode and the impedances between the stylus tip electrode and electrodes, such as the ECG electrodes 30 and/or the back patch 32. The stylus tip electrode location information and the impedance information complement the location and impedance information of the electrodes, such as the ECG electrodes 30 and the back patch 32. This results in a better posed mathematical problem, when solving for the anatomical distribution of heterogeneous complex permittivity, such as when using an EIT algorithm.

In embodiments, to facilitate electrical contact between the stylus tip electrode and the skin of the patient 24, the stylus tip electrode is configured with an absorbent material saturated with an electrically conductive gel. Also, in some embodiments, additional surface electrodes are attached to the patient 24 in locations that are favorable to solving for the anatomical distribution of heterogeneous complex permittivity by, for example, the EIT algorithm. The additional surface electrodes are not permanently connected to the system. Instead, impedance measurements with these additional electrodes are only performed when they are touched by the stylus 28, such that when touched, the system acquires the additional electrode locations based on the magnetically tracked position of the stylus 28, and electrical impedance measurements are acquired at the same time.

The processor 26 determines the model of the impedance tracking field in the three-dimensional shell shape 66, which corresponds to the thorax region of the patient 24, as follows:

The Poisson Equation establishes a relationship between local voltage (V (r)) and charge density. Since, the impedance tracking field frequency is low enough to assume quasi static model behavior, magnetic induction effects are neglected. Under these assumptions, the Poisson Equation in its generalized form is given as:

$$\nabla [\epsilon_c(r) \nabla V(r)] = -\frac{\rho(r)}{\epsilon_0}, \qquad (1)$$

where $\rho$ denotes complex valued charge density and $\epsilon_c$ is the complex permittivity according to:

$$\epsilon_c(r) = \epsilon(r) + \frac{\sigma(r)}{j\omega\epsilon_0}. \qquad (2)$$

Since we expect permittivity and current density to be non-uniform throughout the chest cavity, $E_c$ (r) is a function of location r.

Alternatively, if model accuracy requirements are less stringent, a simpler approximation is a uniform distribution of $E_c$ (r). In this case the Generalized Poisson Equation simplifies to:

$$\nabla^2 V(r) = -\frac{\rho(r)}{\epsilon_c \epsilon_0}. \qquad (3)$$

In the forward solution, a relatively simple method to solve (1) and (3) is the Finite-Difference Method. As its name suggests, it approximates derivatives by finite differences in a discretized model.

Using homogeneous tissue properties, to implement (3), a three-point approximation of the second derivative of V (r) with respect to the x coordinate is:

$$\frac{\partial^2}{\partial x^2} V(r) = \qquad (4)$$

$$\frac{\partial^2}{\partial x^2} V(x_n, y_m, z_k) \approx \frac{V(n-1, m, k) - 2V(n, m, k) + V(n+1, m, k)}{h^2}$$

where n, m, and k are the indices of the discretized computation domain, and h is the grid spacing. Applied to equation (3), and assuming equal grid spacing in all three directions provides:

$$V(n-1, m, k) + V(n+1, m, k) + V(n, m-1, k) + V(n, m+1, k) + \qquad (5)$$

$$V(n, m, k-1) + V(n, m, k+1) - 6V(n, m, k) \approx -\frac{h^2 \rho(r)}{\epsilon_c \epsilon_0}.$$

Solving for V (n, m, k) results in $$V(n, m, k) \approx \qquad (6)$$

$$\frac{1}{6}\Big(V(n-1, m, k) + V(n+1, m, k) + V(n, m-1, k) + V(n, m+1, k) +$$

$$V(n, m, k-1) + V(n, m, k+1) + \frac{h^2 \rho(r)}{\epsilon_c \epsilon_0}\Big).$$

Approximations using a larger number of neighboring points are available as well.

In the Generalized Poisson Equation, in case of a varying electromagnetic tissue properties, the representation of equation (6) has to account for the local $\epsilon_c$ (r) distribution.

Figure 4:
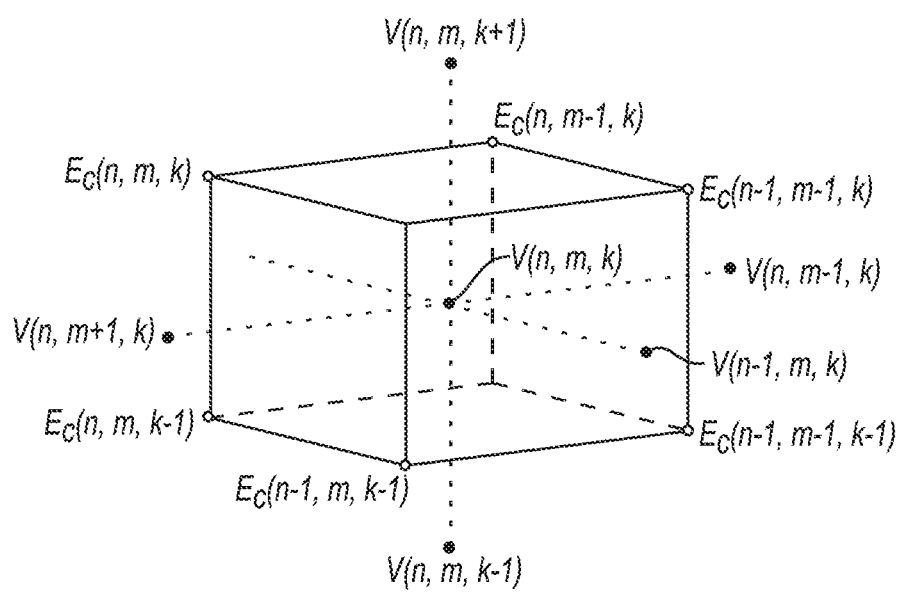
FIG. 4 is a diagram illustrating a computational grid for voltage and the complex permittivity, according to embodiments of the disclosure.

In this scenario, the solution evaluates the finite differences between voltage samples, weighted by the average complex permittivity between them. Following a mathematical derivation similar to the two-dimensional case, the three-dimensional Finite Difference solution of the Generalized Poisson Distribution for V (r) is (compare to FIG. 4):

$$V(n, m, k) \approx \tag{7}$$

$$\frac{1}{a_0}\Big(a_1 V(n-1, m, k) + a_2 V(n+1, m, k) + a_3 V(n, m-1, k) +$$

$$a_4 V(n, m+1, k) + a_5 V(n, m, k-1) +$$

$$a_6 V(n, m, k+1) + \frac{h^2 \rho(r)}{\epsilon_c \epsilon_0}\Big),$$

where $a_0 = \frac{3}{4}(\epsilon_c(n,m,k) + \epsilon_c(n-1,m,k) + \epsilon_c(n,m-1,k) + \epsilon_c(n-1,m-1,k) + \epsilon_c(n-1,m-1,k-1) + \epsilon_c(n,m,k-1) + \epsilon_c(n,m-1,k-1) + \epsilon_c(n-1,m,k-1))$ $a_1 = \frac{1}{4}(\epsilon_c(n-1,m,k) + \epsilon_c(n-1,m-1,k) + \epsilon_c(n-1,m-1,k-1) + \epsilon_c(n-1,m,k-1))$ $a_2 = \frac{1}{4}(\epsilon_c(n,m,k-1) + \epsilon_c(n,m,k) + \epsilon_c(n,m-1,k) + \epsilon_c(n,m-1,k-1))$ $a_3 = \frac{1}{4}(\epsilon_c(n-1,m-1,k-) + \epsilon_c(n-1,m-1,k) + \epsilon_c(n,m-1,k) + \epsilon_c(n,m-1,k-1))$ $a_4 = \frac{1}{4}(\epsilon_c(n-1,m,k-1) + \epsilon_c(n,m,k-1) + \epsilon_c(n,m,k) + \epsilon_c(n-1,m,k))$ $a_5 = \frac{1}{4}(\epsilon_c(n-1,m,k-1) + \epsilon_c(n,m,k-1) + \epsilon_c(n,m-1,k-1) + \epsilon_c(n-1,m-1,k-1))$ $a_6 = \frac{1}{4}(\epsilon_c(n,m,k) + \epsilon_c(n,m-1,k) + \epsilon_c(n-1,m-1,k) + \epsilon_c(n-1,m,k))$ Note that the grids for Cc and V are offset by half the grid spacing, (FIG. 4) i.e. $\in_c$ (n, m, k)=$\in_c$ (xn+h/2, zm+h/2, zk+h/2). This coordinate offset simplifies the mathematical solution and allows for computing electric fields along the boundaries of Cc.

Figure 5:
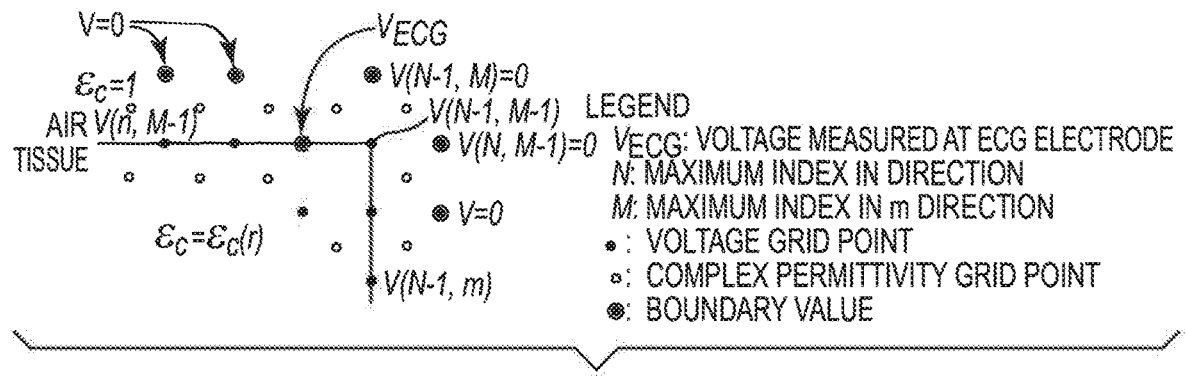
FIG. 5 is a diagram illustrating a finite difference model at the body surface (two-dimensional), according to embodiments of the disclosure.

The boundary conditions of the numerical optimization problem are the voltages measured at the ECG electrodes 30 and the back patch 32, as well as the fact that conductivity outside the body is zero. These scalar measurements and values are referred to as Dirichlet boundary conditions (see FIG. 5).

If an inferior vena cava (IVC) catheter is used, a further boundary condition could be applied to its measurements. However, IVC catheter location is not known a-priori. To apply its measurements as a boundary condition, catheter location can be fixed to a point in the atlas-based anatomical model. This approach is acceptable as long as it is understood that the impedance field approximation provides tracking information that is strictly true only with respect to its atlas-based model.

In some embodiments, the processor 26 is configured to refine the model of the impedance tracking field based on location information and measured field voltages received from a tracking catheter in the patient 24. An impedance tracking field is generated in the patient 24 by injecting currents through the plurality of ECG electrodes 30 to the back patch 32. The tracking catheter measures the field voltages of the impedance tracking field and provides the measured voltages to the processor 26. The processor 26 fits the model of the impedance tracking field to the measured voltages to refine the model. In some embodiments, the tracking catheter is catheter 22. In some embodiments, the tracking catheter is inserted into one of the IVC and the superior vena cava (SVC). In some embodiments, the tracking catheter includes a magnetic tracking system that provides location information about the location of the tracking catheter to the processor 26 along with the measured field voltages.

Figure 6:
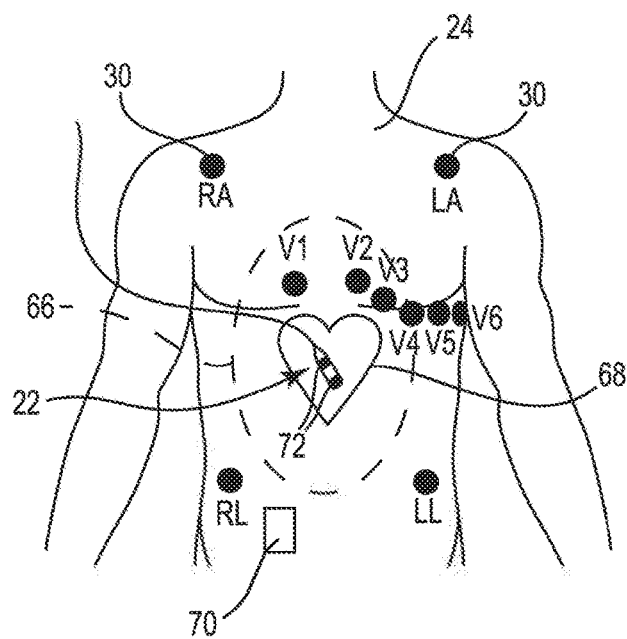
FIG. 6 is a diagram illustrating the catheter in the heart of the patient and the three-dimensional shell shape superimposed on the patient, according to embodiments of the disclosure.

FIG. 6 is a diagram illustrating catheter 22 in the heart 68 of the patient 24 and the three-dimensional shell shape 66 superimposed on the patient 24, according to embodiments of the disclosure. The ECG electrodes 30 (also labeled as RA, LA, RL, LL, V1, V2, V3, V4, V5 and V6) and the back patch 32 (not shown in FIG. 6 for clarity) are attached to the patient 24, as illustrated in FIG. 3A and FIG. 3B. Also, a reference patch 70 is attached to the patient 24 to provide a reference voltage for taking measurements of the impedance tracking field in the patient 24 with electrodes 72 on the catheter 22.

The catheter 22 is a moveable catheter having one or more spatially distributed electrodes 72 at the distal end or near the distal end of the catheter 22. In some embodiments, the catheter 22 is used to perform therapeutic treatments. In some embodiments, the catheter 22 is used to perform ablation, such as RF ablation and/or cryogenic ablation. In some embodiments, the catheter 22 is used to perform diagnostics. In some embodiments, the catheter 22 is used to perform cardiac mapping. In some embodiments, the catheter 22 is inserted into the coronary sinus of the patient 24. In some embodiments, the catheter 22 is used to refine the model of the impedance tracking field based on the location of the catheter 22 and the measured field voltages received from the electrodes 72 of the catheter 22.

The catheter 22 can be fitted with various types of electrodes 72. In some embodiments, the catheter 22 includes one or more ablation electrodes 72 for performing ablation. In some embodiments, the catheter 22 includes at least one pair of CIEs configured to inject electrical current into the medium in which the catheter 22 is disposed. In some embodiments, the catheter 22 includes PMEs to measure the voltages or potentials of the impedance tracking field in the patient 24. In some embodiments, the catheter 22 includes PMEs to measure voltages or potentials resulting from the current injected by the CIEs. In some embodiments, the PMEs are used for cardiac mapping.

The reference patch 70 provides a reference voltage to the processor 26, which is used by the processor 26 as a reference to the measured voltages from the catheter 22. In other embodiments, the processor 26 receives the reference voltage from another source. In some embodiments, the processor 26 receives a system reference voltage from a reference catheter in the patient 24, such as a reference catheter situated in the IVC or the SVC. In some embodiments, the processor 26 receives a system reference voltage from one or more of the plurality of surface electrodes 30. In some embodiments, the processor 26 receives a system reference voltage from the surface patch 32.

In operation, the processor 26 injects current through one or more of the plurality of ECG electrodes 30 to the back patch 32. This creates an electric field in the patient 24, which is the impedance tracking field used to track the location of the catheter 22. With the catheter 22 inserted in the patient 24, such as in the heart 68, electrodes 72 on the catheter 22 measure the field voltages of the impedance tracking field and provide the measured voltages or potentials to the processor 26. The processor 26 receives the measured field voltages, referenced to the reference voltage from the reference patch 70, and performs signal conditioning on the measured voltages as needed.

In some embodiments, the processor 26 performs pre-processing of the measured voltage signals, where the pre-processing includes one or more of noise reduction and filtering.

The processor 26 then fits the measured field voltages from the catheter 22 to the model of the impedance tracking field. In embodiments, the processor 26 matches the measured field voltages to the model of the impedance tracking field. In some embodiments, the processor 26 uses an optimization algorithm to match the measured field voltages to the model of the impedance tracking field and the processor 26 obtains a best fit of the measured field voltages to the model.

After fitting the measured field voltages from the catheter 22 to the model of the impedance tracking field, the processor 26 determines the location of the catheter 22 in the patient 24, such as in the heart 68 of the patient 24. Based on the location of the catheter 22 in the patient 24, determined by the processor 26, medical personnel and/or a physician use the catheter 26 to perform procedures, such as diagnostic, mapping or therapeutic procedures, including ablation.

In embodiments, the processor 26 is configured to detect artifacts and reduce artifacts in the measured field voltages. In some embodiments, the processor 26 is configured to provide noise reduction on the measured field voltages. In some embodiments, the processor 26 is configured to provide respiration gating to obtain the measured field voltages. In respiration gating, as the patient 24 breathes air in and out, the processor 26 measures the field voltages of the impedance tracking filed using the catheter 22 during the same period of the respiratory cycle. In some embodiments, the processor 26 measures the field voltages when the air is out of the patient, since there is more time for measurement when the air is out of the patient 24.

Figure 7:
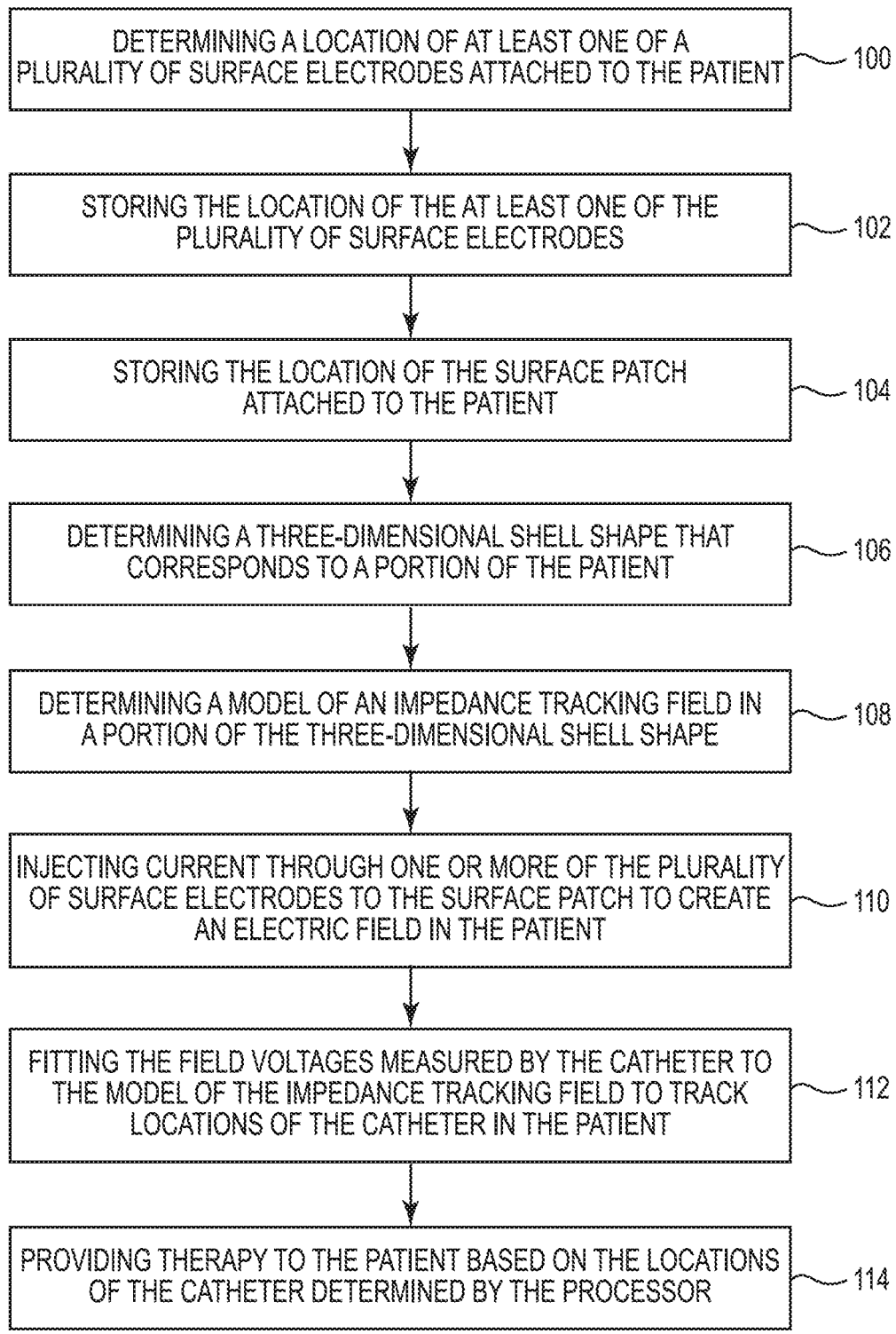
FIG. 7 is a method of tracking a catheter in the patient, according to embodiments of the disclosure.

FIG. 7 is a method of tracking a catheter, such as catheter 22, in the patient 24, according to embodiments of the disclosure. The method is performed by system 20. In other embodiments, the method can be or is performed by a different system.

The method, at 100, includes determining, by the processor 26, a location of at least one of a plurality of surface electrodes 30 attached to the patient 24. Where, in some embodiments, the plurality of surface electrodes 30 is a plurality of ECG electrodes 30. Also, in some embodiments, the method includes determining, by the processor 26, a location of each of the plurality of surface electrodes 30 attached to the patient 24. In some embodiments, the processor 26 determines the locations of other electrodes of the plurality of surface electrodes 30 based on the location(s) of the at least one of the plurality of surface electrodes 30.

Further, in some embodiments, the method includes receiving location information from a stylus, such as stylus 28. The stylus is enabled for tracking a location of the stylus and provides location information to the processor 26 as it is touched to an electrode of the plurality of surface electrodes 30, a surface patch 32, and/or another point on the patient 24.

At 102, the method includes storing, by the processor 26, the location of the at least one of the plurality of surface electrodes 30, and at 104, the method includes storing, by the processor 26, the location of the surface patch 32 attached to the patient 24. The locations can be stored in internal memory of the processor 26 or in memory that is external to the processor 26. In some embodiments, the method includes storing, by the processor 26, the location of each of the plurality of surface electrodes 30. In some embodiments, the method includes storing, by the processor 26, the location of each of the plurality of ECG electrodes 30. Also, in some embodiments, the method includes storing the location of the back patch 32.

Next, the method includes, at 106, determining, by the processor 26, a three-dimensional shell shape 66 that corresponds to a portion of the patient 26. In some embodiments, determining the three-dimensional shell shape 66 includes determining the three-dimensional shell shape 66 based on an ovoid shape, which can include scaling the ovoid shape to fit the locations of the surface electrodes 30 and the back patch 32. In some embodiments, determining the three-dimensional shell shape 66 includes determining the three-dimensional shell shape 66 based on the location of the surface patch 32 and the locations of one or more of the plurality of surface electrodes 30. In some embodiments, determining the three-dimensional shell shape 66 includes determining the three-dimensional shell shape 66 based on locations of other points on the patient 24. In some embodiments, determining the three-dimensional shell shape 66 includes determining the three-dimensional shell shape 66 based on anatomical landmarks in the patient 24, such as anatomical landmarks obtained from an atlas model or from imaging, such as EIT imaging or the like.

At 108, the method includes determining, by the processor 26, a model of an impedance tracking field in a portion of the three-dimensional shell shape 66. In some embodiments, the method includes determining the model based on estimates of electromagnetic tissue properties of the patient 24. In some embodiments, the method includes determining the model based on estimates of electromagnetic tissue properties of the patient 24 that include constant gradients across the patient 24. In some embodiments, the method includes determining the model based on estimates of electromagnetic tissue properties of the patient 24 including estimates of the locations of organs in the patient 24. In some embodiments, the method includes determining the model based on estimates of electromagnetic tissue properties of the patient 24 based on EIT imaging or the like. In some embodiments, the method includes determining the model based on estimates of electromagnetic tissue properties of the patient 24 including measured field voltages from a tracking catheter and magnetically obtained locations of the tracking catheter in the patient 24.

In tracking the catheter, at 110, the method includes injecting current, by the processor 26, through one or more of the plurality of surface electrodes 30 to the surface patch 32 to create an electric field in the patient 24. This electric field is the impedance tracking field that is subsequently detected and measured by electrodes on the catheter, such as electrodes 72 on the catheter 22, inserted into the patient 24.

At 112, the method includes fitting, by the processor 26, the field voltages measured by the catheter to the model of the impedance tracking field to track locations of the catheter in the patient 24. In some embodiments, the processor 26 matches the measured field voltages to the model of the impedance tracking field. In some embodiments, the processor 26 uses an optimization algorithm to match the measured field voltages to the model of the impedance tracking field and the processor 26 obtains a best fit of the measured field voltages to the model.

In embodiments, after fitting the measured field voltages from the catheter to the model of the impedance tracking field, the processor 26 determines the location of the catheter in the patient 24, such as in the heart 68 of the patient 24. Based on the location of the catheter in the patient 24, medical personnel and/or a physician use the catheter to perform procedures, such as diagnostic, mapping and/or therapeutic procedures, such as therapeutic procedures that include ablation.

At 114, the method includes providing, by the processor 26, therapy to the patient based on the locations of the catheter determined by the processor 26.

Also, in some embodiments, the method includes detecting and reducing artifacts in the measured voltages, such as by providing noise reduction to the measured field voltages and/or providing respiration gating while obtaining the measured field voltages.

The systems and methods describe herein reduce or eliminate the need to first create a map of the impedance tracking field in the region of interest in the patient 24. This reduces the cost of performing procedures, such that less complex procedures that do not justify the time or money needed for mapping the region of interest can be performed. Also, the system and methods described herein do not use fluoroscopy, such that exposure to excessive x-rays is reduced.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the above described features.

We claim:

1. A system for tracking a catheter in a patient comprising:
a plurality of surface electrodes attached to the patient;
a surface patch attached to the patient;
a stylus including a magnetic tracking system for a location of the stylus within a magnetic field; and
a processor coupled to the stylus, the plurality of surface electrodes and the surface patch, the processor configured to:
determine a location of at least one of the plurality of surface electrodes based on the location of the stylus;
store a location of the surface patch and the location of the at least one of the plurality of surface electrodes;
determine a three-dimensional shell shape that corresponds to a portion of the patient;
determine a model of an impedance tracking field in at least a portion of the three-dimensional shell shape;
inject current through one or more of the plurality of surface electrodes to create an electric field in the patient;
fit measured voltages from the catheter to the model of the impedance tracking field to determine locations of the catheter in the patient; and
provide therapy to the patient based on the locations of the catheter.

2. The system of claim 1, wherein the plurality of surface electrodes is a plurality of electro-cardiogram electrodes attached to the patient.

3. The system of claim 1, wherein the processor is configured to determine the three-dimensional shell shape based on one or more of an ovoid shape, the location of the surface patch and the location of the at least one of the plurality of surface electrodes, locations of multiple points on surfaces of the patient, and anatomical landmarks in the patient.

4. The system of claim 1, wherein the processor is configured to determine the model of the impedance tracking field based on estimates of electromagnetic tissue properties of the patient.

5. The system of claim 4, wherein the estimates of electromagnetic tissue properties of the patient are based on at least one of constant gradients across the patient, estimates of locations of organs in the patient, and electrical impedance tomography imaging of the patient.

6. The system of claim 4, wherein the processor is configured to refine the model of the impedance tracking field based on at least one of measured voltages from a tracking catheter and magnetically obtained locations of the tracking catheter in the patient.

7. The system of claim 1, wherein the processor is configured to receive a system reference voltage that is used to obtain the measured voltages from the catheter, the system reference voltage received from at least one of a reference catheter in the patient, a reference patch attached to the patient, one or more of the plurality of surface electrodes, and the surface patch.

8. The system of claim 1, wherein the processor is configured to provide respiration gating to fit the measured voltages from the catheter to the model of the impedance tracking field to determine the locations of the catheter in the patient.

9. A system for tracking a catheter in a patient comprising:
a plurality of electro-cardiogram electrodes attached to the patient;
a surface back patch that includes a magnetic tracking system that provides location information about a location of the surface back patch on the back of the patient;
a stylus that is enabled for tracking a location of the stylus; and
a processor coupled to the plurality of surface electrodes, the surface back patch, and the stylus, the processor configured to:
determine locations of the plurality of electro-cardiogram electrodes from location information obtained from the stylus;
determine the location of the surface back patch from the location information from the surface back patch;
store the locations of the plurality of electro-cardiogram electrodes and the location of the surface back patch;
determine a three-dimensional shell shape that corresponds to a portion of the patient based on the locations of the plurality of electro-cardiogram electrodes and the location of the surface back patch;
determine a model of an impedance tracking field in at least a portion of the three-dimensional shell shape;
inject current through one or more of the plurality of electro-cardiogram electrodes to create an electric field in the patient;
fit measured voltages from the catheter to the model of the impedance tracking field to determine locations of the catheter in the patient; and
provide therapy to the patient based on the locations of the catheter.

10. The system of claim 9, wherein the processor is configured to determine the three-dimensional shell shape based on one or more of an ovoid shape, locations of multiple points on surfaces of the patient, and anatomical landmarks in the patient.

11. The system of claim 9, wherein the processor is configured to determine the model of the impedance tracking field based on estimates of electromagnetic tissue properties of the patient including one or more of constant gradients across the patient, estimates of locations of organs in the patient, and electrical impedance tomography imaging of the patient.

12. The system of claim 9, wherein the processor is configured to receive a system reference voltage obtained from one or more of a reference catheter in the patient, a reference patch attached to the patient, one or more of the plurality of surface electrodes, and the surface patch.

13. A method of tracking a catheter in a patient comprising:
  receiving, by a processor, a signal transmitted from a stylus indicating a location of the stylus;
  determining, by a processor and based on the signal received from the stylus, a location of at least one of a plurality of surface electrodes attached to the patient;
  storing, by the processor, the location of the at least one of the plurality of surface electrodes;
  storing, by the processor, a location of a surface patch attached to the patient;
  determining, by the processor, a three-dimensional shell shape that corresponds to a portion of the patient;
  determining, by the processor, a model of an impedance tracking field in at least a portion of the three-dimensional shell shape;
  injecting, by the processor, current to one or more of the plurality of surface electrodes to create an electric field in the patient;
  fitting, by the processor, measured voltages from the catheter to the model of the impedance tracking field to track locations of the catheter in the patient; and
  providing, by the processor, therapy to the patient based on the locations of the catheter.

14. The method of claim 13, wherein storing the location of the surface patch includes obtaining location information from a tracking system in a surface back patch, and wherein determining the location of the at least one of a plurality of surface electrodes includes determining, by the processor, a location of at least one of a plurality of electro-cardiogram electrodes attached to the patient.

15. The method of claim 13, wherein determining, by the processor, the three-dimensional shell shape includes determining the three-dimensional shell shape based on one or more of an ovoid shape, the location of the surface patch and the location of the at least one of the plurality of surface electrodes, locations of multiple points on surfaces of the patient, and anatomical landmarks in the patient.

16. The method of claim 13, wherein determining, by the processor, the model of the impedance tracking field in at least a portion of the three-dimensional shell shape, includes determining the model based on estimates of electromagnetic tissue properties of the patient that include one or more of constant gradients across the patient, estimates of locations of organs in the patient, electrical impedance tomography imaging of the patient, measured voltages from a tracking catheter and magnetically obtained locations of the tracking catheter in the patient.

17. The method of claim 13, wherein the processor 26 is configured to provide respiration gating while obtaining the measured voltages from the catheter.

* * * * *